United States Patent
Rapaka et al.

(10) Patent No.: US 10,350,434 B2
(45) Date of Patent: Jul. 16, 2019

(54) PATIENT-SPECIFIC RADIATION DOSE ASSESSMENT IN MEDICAL THERAPY

(71) Applicant: Siemens Healthcare GmbH, Erlangen (DE)

(72) Inventors: Saikiran Rapaka, Pennington, NJ (US); Stefan Kluckner, Berlin (DE); Carol Novak, Newtown, PA (US); Puneet Sharma, Princeton Junction, NJ (US); Dorin Comaniciu, Princeton Junction, NJ (US)

(73) Assignee: Siemens Healthcare GmbH, Erlangen (DE)

(*) Notice: Subject to any disclaimer, the term of this patent is extended or adjusted under 35 U.S.C. 154(b) by 111 days.

(21) Appl. No.: 14/966,484

(22) Filed: Dec. 11, 2015

(65) Prior Publication Data

US 2017/0165501 A1 Jun. 15, 2017

(51) Int. Cl.
*A61N 5/10* (2006.01)
*G06T 19/00* (2011.01)
*G06T 7/73* (2017.01)

(52) U.S. Cl.
CPC ......... *A61N 5/1031* (2013.01); *A61N 5/1049* (2013.01); *G06T 7/73* (2017.01); *G06T 19/006* (2013.01); *A61N 5/1071* (2013.01); *A61N 2005/1034* (2013.01); *A61N 2005/1059* (2013.01); *G06T 2207/10116* (2013.01); *G06T 2207/30004* (2013.01); *G06T 2207/30196* (2013.01)

(58) Field of Classification Search
CPC ........... A61B 6/542; A61B 6/00; A61B 6/488; A61B 6/545; A61B 6/5235; A61B 6/548
USPC ............................................ 378/97, 98.2, 96
See application file for complete search history.

(56) References Cited

U.S. PATENT DOCUMENTS

| | | | |
|---|---|---|---|
| 2012/0148131 A1* | 6/2012 | Couch | A61B 6/032 382/131 |
| 2013/0083004 A1* | 4/2013 | Nord | A61N 5/1031 345/419 |
| 2016/0175614 A1* | 6/2016 | Taguchi | A61N 5/1049 382/131 |
| 2016/0193480 A1* | 7/2016 | Ribbing | A61N 5/1001 600/3 |
| 2016/0287906 A1* | 10/2016 | Nord | A61N 5/103 |

OTHER PUBLICATIONS

Hissoiny, Sami, et al. "GPUMCD: A new GPU-oriented Monte Carlo dose calculation platform." Medical physics 38.2 (2011): 754-764.

(Continued)

*Primary Examiner* — Don K Wong (57) ABSTRACT

In order to provide radiation dose estimation during a treatment, one or more characteristics of the patient are used. A camera captures the patient so that the characteristics (e.g., organ position) may be derived. Radiation exposure and/or absorption are determined from the characteristics. A Monte Carlo, machine-learnt, or other model estimates the dosage for different locations in the patient. During the treatment, the dosage may be presented as a warning when exceeding a threshold or other visualization.

14 Claims, 3 Drawing Sheets

(56) References Cited

OTHER PUBLICATIONS

Hissoiny, Sami, et al. "Sub-second high dose rate brachytherapy Monte Carlo dose calculations with bGPUMCD." Medical physics 39.7 (2012): 4559-4567.

Jia, Xun, Peter Ziegenhein, and Steve B. Jiang. "GPU-based high-performance computing for radiation therapy." Physics in medicine and biology 59.4 (2014): R151.

Su, Lin, et al. "ARCHERRT—A GPU-based and photon-electron coupled Monte Carlo dose computing engine for radiation therapy: Software development and application to helical tomotherapy." Medical physics 41.7 (2014): 071709.

\* cited by examiner

PATIENT-SPECIFIC RADIATION DOSE ASSESSMENT IN MEDICAL THERAPY

BACKGROUND

The present embodiments relate to dose assessment. While medical therapy using ionizing radiation has been a boon for many clinical applications, there are risks. The exposure of healthy tissue to radiation should be limited. To this end, radiation dosage is carefully planned. It is important that the energy from ionizing radiation be deposited in cancerous cells, with minimum exposure to normal, healthy cells. Existing methods of estimating exposure include modeling the dose output by the x-ray or measuring the radiation with dosimeters at the skin of the patient, but these approaches are not patient-specific and provide little information on spatial localization of the absorbed radiation. The absorbed dosage depends of the size and age of the patient, the size of the organ, the x-ray source properties, and scanning protocol used.

Computational models based on the Monte-Carlo methods may provide a more patient-specific estimate of dose. The model may take minutes or hours to solve, so it is not applied during routine clinical practice.

BRIEF SUMMARY

By way of introduction, the preferred embodiments described below include methods, systems, instructions, and computer readable media for assessment of radiation dose. In order to provide dose estimation during a treatment, one or more characteristics of the patient are used. A camera captures the patient so that the characteristics (e.g., organ position) may be derived. Radiation exposure and/or absorption are determined from the characteristics. A Monte Carlo, machine-learnt, or other model estimates the dosage for different locations in the patient. During the treatment, the dosage may be presented as a warning when exceeding a threshold or other visualization.

In a first aspect, a method is provided for assessment of radiation dose. An x-ray source applies radiation directed to a region in a patient over a treatment period of a therapy appointment. An anatomy position of anatomy of the patient is estimated. Dosage at the anatomy of the patient is modeled during the treatment period. The modeling uses the anatomy position. A visualization of the dosage is presented during the treatment period.

In a second aspect, a non-transitory computer readable storage medium has stored therein data representing instructions executable by a programmed processor for assessment of radiation dose. The storage medium includes instructions for: estimating the radiation dose applied from a radiation source to an organ adjacent a treatment location of a patient, the estimating occurring while the radiation source applies radiation to the patient and using a machine-learnt or Monte Carlo model; and transmitting the radiation dose while the radiation source applies the radiation.

In a third aspect, a system is provided for assessment of radiation dose. An x-ray source is configured to apply radiation to a patient. A camera is configured to image the patient during application of the radiation. A processor is configured to estimate locations of organs based, at least in part, on the image from the camera, and to model dosage of the organs during the application of the radiation using the locations. A display is configured to display the dosage for at least one of the organs.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Patient-specific radiation dose assessment and visualization is provided. First, a patient-specific anatomical feature extraction is performed. Then, a model-based radiation dose assessment is made based, in part, on the feature extraction. Finally, the dose is visualized, such as presenting an in-patient, see-through view using augmented reality devices.

In one embodiment, the model-based radiation dose assessment is made patient specific using the extracted anatomical features. To provide the assessment and visualization during treatment, the modeling is performed with parallel processing and/or a machine-learnt classifier.

Figure 1:
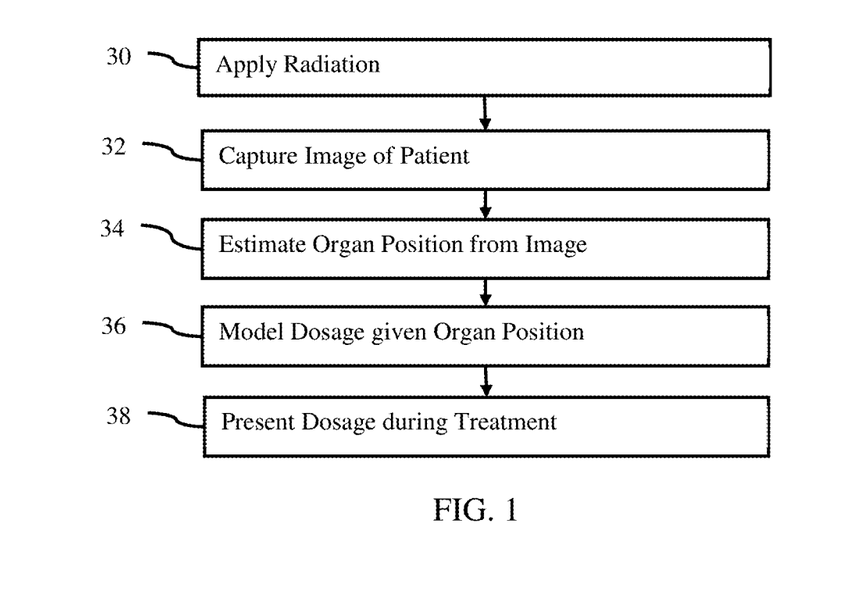
FIG. 1 is a flow chart diagram of one embodiment of a method for assessing dosage of medical therapy.

FIG. 1 shows a method for assessment of radiation dose. The radiation dose applied from a radiation source to an organ or organs adjacent to a treatment location of a patient is estimated. Any resolution may be used, such as organ level dose determination or smaller voxel level dose determination. The estimation relies, at least in part, on patient specific information, such as organ position. This patient-specific information is used to estimate dosage for parts of the patient where exposure to the radiation is to be kept below a threshold.

Figure 5:
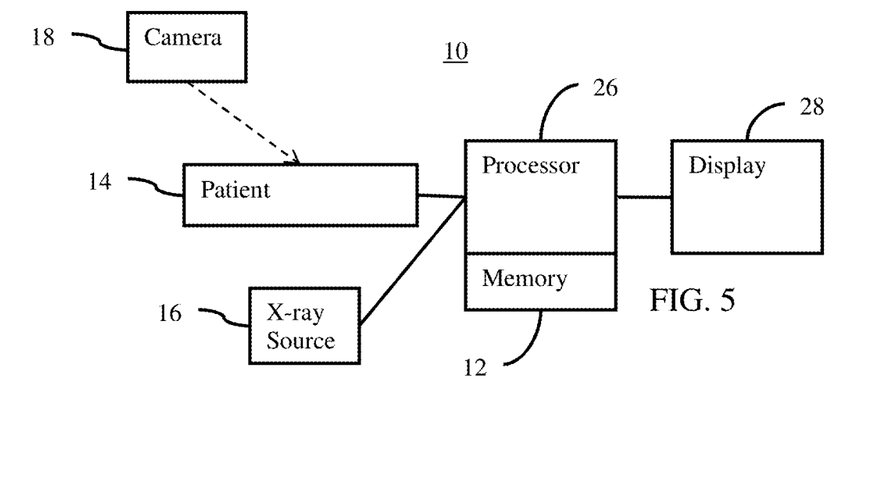
FIG. 5 is a block diagram of one embodiment of a system for assessing dosage for medical therapy.

The method is implemented by the system 10 of FIG. 5 or another system. An x-ray source applies the radiation. A camera or cameras may capture an image or images used to determine patient specific information, such as likely location of organs relative to the x-ray source. A processor estimates the organ position and models the dosage at the organ or organs. A display presents the dosage as a function of space and/or time.

The acts are performed in the order shown or other orders. For example, acts 32 and/or 34 are performed prior to act 30.

Additional, different, or fewer acts may be provided. For example, the output act 38 is not provided, but instead the determined dose is used to modulate the application of act 30. As another example, input of patient specific information not captured by the camera, such as the age of the patient, is input.

In act 30, a source applies radiation. The source is an x-ray source applying ionized radiation, but other radiation sources may be used. In one embodiment, the x-ray source is supported by a C-arm. The C-arm moves the x-ray source to different positions relative to the patient for concentrating exposure of a treatment location or lesion to radiation while minimizing exposure of organs. Other structures may support the x-ray source while allowing movement of the source relative to the patient. Alternatively, the x-ray source is fixed or held in position while the patient is moved.

The radiation is applied to a lesion in a patient. The lesion may have any shape or size. The lesion is on, in, by, adjacent to, or spaced from any number of organs. The radiation is applied to damage the lesion while minimizing exposure of the organs. A collimator, intensity modulation, change in orientation, and/or dwell time at any given position may be used to apply sufficient radiation for treatment while minimizing or reducing exposure for other locations. Any radiation treatment procedure may be used.

The radiation is applied during a treatment period of a therapy appointment. The radiation treatment procedure may include one or more different treatment periods or appointments, such as separately exposing the patient to radiation on different days. For a given appointment, the treatment procedure may include various stops and starts of radiation application, such as to allow the source of the radiation to be repositioned relative to the patient and/or to allow the patient to breath or stop holding their breath periodically during the treatment period. A given treatment period corresponds to a given treatment appointment. For example, a treatment period is two hours or less time.

In act 32, a camera captures an image or images of the patient. More than one camera may capture an image or images. Any now known or later developed camera may be used, such as a charge coupled device (CCD) camera with any resolution. In one embodiment, a depth camera is used. The depth camera may include a source of structured light, multiple cameras for stereo viewing, and/or a red green blue-depth (RGB-D) camera that senses depth to a nearest surface for each pixel in an image.

The camera has a known position relative to the x-ray source. The position may be known due to the camera have a fixed spatial position relative to a base of the C-arm. The position may be known through calibration and/or registration. For example, the camera is part of a mobile device with an included magnetic position sensor that provides location measurements in six degrees of freedom. The position and orientation of the camera is detected in a coordinate system that may be related to the coordinate system of the x-ray source.

By having a measured or known position relative to the x-ray source, the position of the patient relative to the x-ray source is determined. The image or images captured by the camera indicate the position of the surface of the patient relative to the camera, which has a known position relative to the x-ray source. The coordinate systems may be aligned or the position of one device or object may be determined in other coordinate systems.

Figure 2:
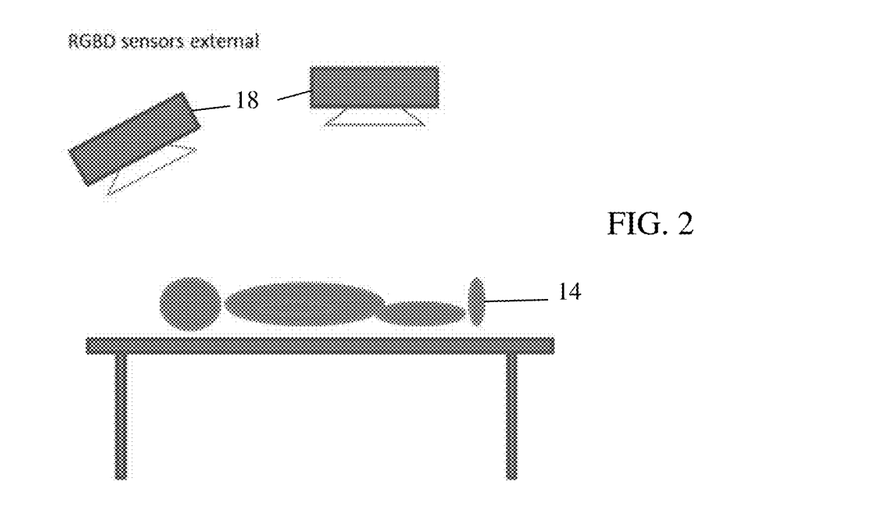
FIG. 2 illustrates an example of cameras relative to a patient for determining patient characteristics for dosage estimation.

FIG. 2 shows an example of two cameras 18 positioned to capture an image or images of a patient 14. The image is captured prior to, during, and/or after the application of radiation. At some point in the therapy appointment, one or more images are captured, such as capturing in real-time with the application of radiation. Where the image is used just to derive a characteristic of the patient, one image may be used at any time. Where the imaging is used to determine current patient position for registration with the x-ray source and/or display device, a sequence of images may be captured, including images during the application of radiation.

The image represents a surface of the patient. The patient may be naked, so the image represents the skin of the patient. Alternatively, the patient has a robe or other clothing, so the image represents a surface of the patient as distorted by the clothing.

With or without clothing, the image captures anatomical features of the patient. The features may be the shape, size, and/or location of the patient or parts of the patient. For example, using a detected neck region and crotch or head and feet, a height of the patient is determined. A width of the torso may be determined. The age may be derived from the image, such as by using facial information. Distances between points, areas, and/or volumes may be captured or represented on the image.

In alternative embodiments, medical scan data is acquired. The scan data is used instead of an optical or other camera. The scan data provides spatial distribution information, so may be used instead of an image from the camera.

Other information specific to a patient may be input from the user and/or accessed from a medical record. For example, the body mass index, age, weight, or other characteristic of the patient is determined separately from image capture.

In act 34, a processor estimates an anatomy position of anatomy of the patient from the image or images. Any anatomy, such as the entire patient or more specific (e.g., organ or organs) is estimated. The positions of one or more organs may be estimated. The organ or organs are different from the lesion or lesions being treated. The lesion or may be on or part of the organ, but the position of healthy organ tissue or organs not to be treated are estimated. The organ position may be determined as voxels flagged as being part of the organ. Alternatively, the volume of the organ is determined as being the organ.

Where multiple images are captured at the same time, an average position may be used. Alternatively, the information from the different images are fit to or unified in a model or one representation of the surface of the patient at a time.

In one embodiment, the position of an organ is based on the position of the patient. The patient pose (i.e., position and orientation) indicate the relative position of one or more organs. The position of the patient in an image indicates the position of the organs at the time of image capture.

Figure 3:
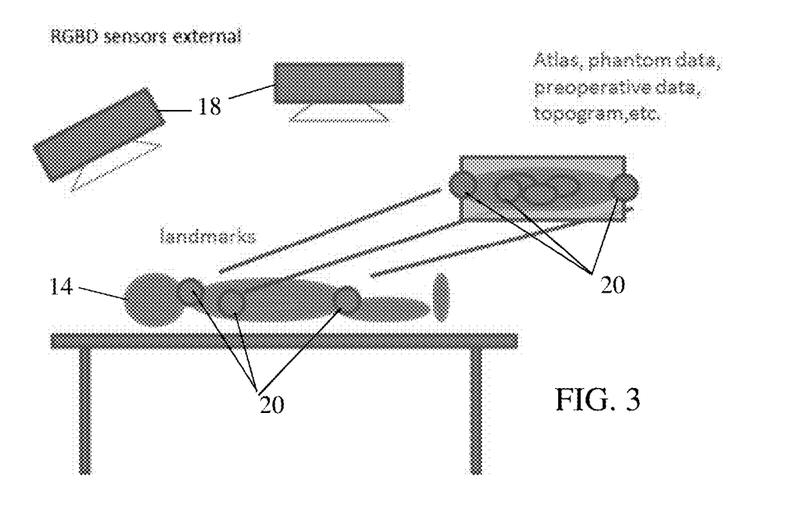
FIG. 3 illustrates the example of FIG. 2 with landmarks.

In another embodiment, the position of the organ is derived from landmarks represented in and identified from the image. The processor identifies one or more landmarks in the image to understand the patient pose. FIG. 3 shows an example where the landmarks 20 are the shoulders, neck, and hip joints. Other landmarks 20, such as the head, hand, ribs, stomach, knees, other joints, or other surface locations, may be found.

The landmarks 20 are found by image processing. For example, a model of a patient at different poses is fit to the surface measured with the camera. The model includes labels for the landmarks, so fitting (e.g., affine transform) to the image data provides landmarks 20 for the specific patient. In other embodiments, a pattern or template of a landmark or group of landmarks is tested at different positions relative to the image. The position with the best match indicates the location of one or more landmarks 20. In yet another approach, a machine-learnt classifier is trained to identify one or more landmarks from the input image. Other image processing to identify landmarks may be used.

The landmarks 20 together represent the patient pose. Alternatively, different landmarks 20 are used in one or more unique combinations to determine organ positions. Since the position of the camera relative to the x-ray source is known, a transform or vector may be used to determine the position of the landmarks 20 relative to the x-ray source.

The processor determines the patient pose and/or organ positions relative to the radiation source. In one embodiment, the pose and/or size of the patient are determined from the captured image. The position of an organ is estimated from the pose and size. The organ position may be based on the size of the patient. For example, the height of the patient determines the likely location of the organ. The pose of the patient also determines the likely location. The size information may also indicate the size of the organ. The size of the organ effects the organ position as some locations may include the organ if larger while an organ for a smaller patient is not at that those locations. The landmarks 20 are used to directly estimate the organ position and/or indirectly through the patient pose and/or size.

An atlas or representative information may be used to estimate the organ position relative to the x-ray source. The atlas indicates organ position relative to landmarks for a typical patient. Other information than just the landmarks or image-derived information may be used. For example, based on the size, age, and other anatomical features (e.g., landmarks 20) of the patient, an initial assessment is made of the different organ positions and the organ sizes. This estimate may be based, in part, on atlases from previously known patient anatomies, phantom data, or other databases. One possibility is to use an annotated database of previously scanned patients to learn organ sizes for patients of different ages and/or sizes. A look-up table indexed by patient size and age is used to determine organ position relative to the patient. The patient pose is then used to reference the determined organ position to the x-ray source.

Other indicators of organ position may be used to determine the organ position. For example, the C-arm and x-ray source are used with a detector to acquire a topogram. Computer tomography is used to reconstruct a representation of the interior of the patient from a scout scan. This interior representation may represent different organs, which may be segmented or identified, but may not due to low power of the scout scan. The organ position relative to the patient is determined and used alone or in combination (e.g., averaging) with the organ position derived from the captured images of the exterior of the patient.

The organ position is determined once, such as determined during the treatment (e.g., while the patient is lying on the patient bed as part of an appointment or while being exposed to radiation). The organ position is used for subsequent dosage estimation. Alternatively, the organ position is periodically, regularly, or occasionally determined. Throughout the appointment or application of radiation, the patient may shift position. To deal with this motion, the organ position is estimated at different times using different images captured for those times.

In act 36, the processor models the dosage at the organ or organs of the patient during the treatment period. As the dose is being applied, in between application but still during the appointment, and/or while the patient is continuously on the bed, the processor computes the dosage per location. The modeling occurs prior to termination of the treatment period so that the dose applied to a given organ or organs may be monitored. The modeling is based on applying the radiation in the treatment period up to a time of the modeling. For a given time of modeling, the model accounts for the dose applied from the beginning of the treatment period to the time of modeling. Alternatively, the modeling is for dosage over any unit time. In other embodiments, the modeling occurs prior to or after application.

The therapy parameters (e.g., intensity, orientation, and filtering or collimation) are used to estimate the dose per organ or unit volume. The dosage may be computed for different organs or for parts of organs, such as computing the dosage per voxel. Based on the scanner and protocol parameters, a model may be used to estimate the dosage received by different organs. This model may have varying degrees of fidelity, depending upon the desired accuracy and processing time requirements. For instance, for planning radiation therapy and designing suitable filters, a higher fidelity model may be used. For interventional applications providing immediate results or results while the treatment continues, some fidelity may be sacrificed for faster performance. Fidelity is sacrificed by increasing the voxel size and/or replacing some calculations with assumptions or simplifications.

The modeling uses the organ position. The model accounts for attenuation, absorption, or other factors along the path of travel. By knowing the organ position, the radiation applied to the organ and/or along paths of travel is estimated. Due to collimation, intensity, and orientation, different paths of travel at a given time are subjected to different amounts of radiation. The organ position is used to determine an amount of radiation per voxel or organ for each unit time. Where the types of tissue are known or estimated, the type of tissue may be used to determine the absorption of the radiation along the path and/or at the organ or organs of interest. The model accounts for fewer, additional, or different factors to estimate dose for the organ. The organ position is used to determine the amount of radiation to which the organ is subjected.

In one embodiment, the dose is modeled with a Monte-Carlo model. A Monte-Carlo based method simulates individual particle trajectories with appropriate physics to emulate the scanning protocol. For instance, Monte Carlo methods use photon-only models, electron models, or combined photon-electron models. Other particle or wave modeling may be used. Alternatively, a grid-based technique solves effective equations, such as the Boltzmann equation or Fokker-Planck equation, on grids instead of simulating individual particle trajectories. These physics based models may account for different scanner properties, such as the energy spectrum of the radiation source and any filters or source current alterations used during the acquisition.

For the Monte-Carlo or other physics-based model, parallel processing is used to provide estimates of dose during the treatment period. Parallel architectures, such as graphical processing units (GPUs), multi-core processor, and/or other co-processors provide computational acceleration, allowing solution of the physics-based model within a minute or less. In an additional or alternative approach, some or all of the computational process is performed by a network of computers utilizing an on-demand computing infrastructure. The network may be an offsite (e.g., cloud computing) or on-site grid of computers.

For more rapid estimation of the dose, the modeling may use a machine-learnt classifier. The physics-based modeling (e.g., Monte-Carlo model) may be used to train a classifier. For instance, a physics-based model is run on a large database of patient or synthetic anatomies, using different scanner parameters. The results of the many physics-based simulations generate an enormous amount of data, upon which a machine-learning model is trained using appropriately selected feature vectors to represent the anatomical features, the scanner parameters, and the protocol parameters. Once the trained model is available, the machine-learnt model is used for a given patient to provide fast estimates of the different organ-level doses. The machine-learnt classifier estimates dose by location given various inputs, such as the organ position, patient age, and scanner and protocol parameters, for a specific patient.

Nearly real-time estimates (e.g., within five seconds or less) of radiation dosage are provided, but without the same number of computations as using physics-based modeling in real time. This approach offloads the bulk of the computational effort to the offline training process, resulting in nearly instantaneous prediction for unseen data. For estimation during treatment, the protocol information up to that point is applied in the input feature vector. The model outputs estimates of dose based on the treatment up to that point.

Other modeling may be used. Combinations of physics-based modeling and machine learnt modeling may be used. The processor models the dose for healthy tissue, such as organs not being treated yet exposed to some radiation due to the treatment of a lesion.

The dose may be any quantity representing radiation exposure. For instance, maximum local exposure, average exposure per organ, locations of peak energy deposition, or other metrics may be calculated. Transient exposure information, such as the dosage received by an organ as a function of time, may be calculated. The metric or metrics are calculated for each voxel, but may instead be calculated for each organ. For example, the maximum, average, total, or other measure is calculated for an organ. The dose measures of the voxels representing the organ are combined for the organ-specific calculation.

In act 38, the processor creates a visualization of the dosage on a display. The display presents the visualization of the dose. Since the processor estimates the dose during the treatment period, the visualization of the dose may be presented during the treatment period. At least once, periodically, when triggered, or at any frequency, the user is presented with the visualization to monitor the dose applied. Since the presentation is during the treatment period, the monitoring occurs at a time at which the dose to healthy tissue is critical. While planning may avoid excessive dose to healthy tissue, the planning may not account for patient movement, organ position, or organ size. By capturing the patient in the camera and using real-time position of the patient and organs in the dose estimation, the visualization may be used in real-time with the treatment to assure excessive dose does not occur. In alternative embodiments, the visualization is presented prior to or after the treatment period.

Any visualization may be used. In one embodiment, an image representing the dosage is generated. The image is a three-dimensional rendering of the interior of the patient. The color for the voxels used in the rendering is modulated by the doses for the voxels. The resulting rendering is a two-dimensional image representing the volume with pixels colored based on the amount of dose. Alternatively or additionally, one or more two-dimensional cross-sectional images are generated.

Interactivity may be provided for altering clip planes, view direction, color maps, or other rendering. The interactivity may alter cross-sectional plane position. A mouse, keyboard, gesture control, touch-enabled devices (e.g., tablet or touch screen), voice commands at a microphone, or other input device or technique may be used to interact with the visualization.

The image is provided on a computer monitor, workstation, or other display. For smart phones or tablets, cloud-based rendering and storage may be used to create the visualization presented on the phone or tablet.

In other embodiments, the visualization is a warning. Rather than or in addition to an image, an alert or other warning is output. The warning is visual, but may instead or also be audial. The warning is presented when the dosage for any healthy tissue is at or above a threshold. Different thresholds may be used for different locations, such as for different organs. The warning is a red flag or notice that excessive dose for an organ is close to a pre-set limit. When presented during the treatment period, the treatment may be halted or altered to account for the dose to the organ.

The response to the warning may be manual. Alternatively, the response is automatic. The processor causes the treatment to cease or alters the treatment (e.g., reduce dwell time at a particular orientation or alter the collimation) in response to the warning.

Figure 4:
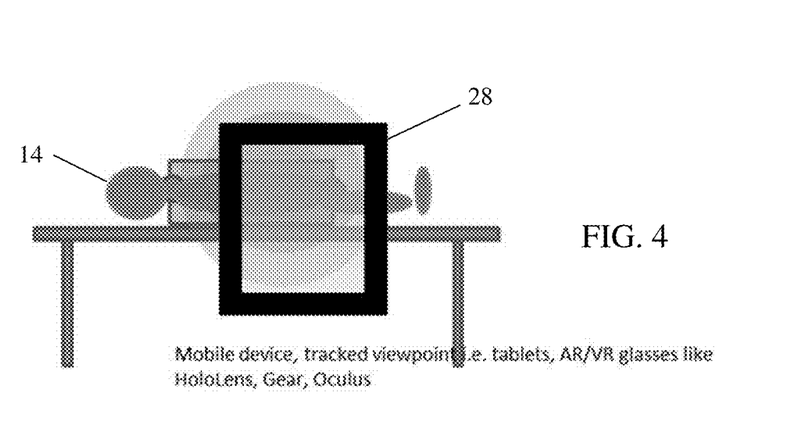
FIG. 4 shows an example augmented reality presentation.

In yet another embodiment, the dose is presented in an augmented reality view of the patient. An image and/or warning are presented on a display as overlaid with a view from the user's perspective. The view may use purpose-built augmented reality devices (e.g., Oculus Rift, Samsung Gear VR, or Microsoft HoloLens) or may be on any display (e.g., smart phone or tablet) with a known or measured orientation.

In augmented reality, a portion of the user's view is replaced with the augmentation. The augmentation may be an overlay on the view of the user, such as overlaying dose information on a view of a surface of the patient. To enhance the visualization, the augmentation may be presented as if part of the patient is see-through. The see-through technique enables the joint continuous visualization of the body hull and internal body structures at various levels of detail. FIG. 4 shows an example where the user's view is of the entire patient 14, but a display 28 adds augmented dose and internal structure information in a see-through presentation. The estimated organ position and dose are used to generate a rendering with transparency for augmenting part of the user's view.

In the augmented reality with a see-through view, calibration, registration, and visualization are used. Calibration aligns the coordinate system of the display and that of the scanner and/or camera. During registration, the captured body surface model is aligned with the scanner modality, and the display is aligned with the body surface. Once the subject scan is loaded to the system, the detected landmarks are associated to the corresponding landmarks on the scanner modality. Upon successful registration, the model results are viewed live on the display. After calibration and registration, interactive exploration is provided with the augmented reality display.

To compensate the registration errors from inaccurate landmark detection results, a parameterized deformable mesh (PDM) model may be applied to correct the landmark locations. Compared to landmark detectors trained with local features, PDM leverages global shape information and generates an optimal avatar mesh that closely fits to the skin surface of the subject. Landmark errors due to noisy input data (e.g., clothing and sensor noise) may be reduced.

The computed affine transformation between the detected landmarks and the camera are used to set up the virtual camera used to render the image with the correct orientation, scaling, and projection in the augmented view. The relative pose between origin and the current pose of the position-sensing device is used to update the viewpoint of the rendering scene.

In one embodiment, the image captured by the camera is used to construct a color point cloud or surface object(s). The live or real-time color information is mapped to the point cloud or surface with varying opacity. The constructed object(s) are added to a rendering scene together with an image of the patient from the camera or a scanner. Such a rendering scene produces a three-dimensional view with the effect of the live object hull enclosing the scan modality data (e.g., data from the topogram or atlas). The scan modality data may be rendered as a direct image of the volume or as extracted surface structures with or without texture values sampled from the scanner or atlas.

The rendered view may be overlaid onto the live image to produce the see-through effect. Optionally, the corresponding landmarks of the live object hull are used as anchor points to deform the texture coordinates of the scanner image or atlas. In a simpler approach, the construction of the hull is skipped, and the scan modality or atlas is overlaid onto the live camera image directly rendered according to the detected pose.

Rendering is performed on a local display system or using streaming technologies in a client-server architecture. Rendering by a server may allow for higher quality rendering. In the server case, the local client processor may decode a compressed image stream already rendered and encoded at the server.

Other visualizations may be presented. For example, a graph or chart of dose is output. As another example, a dose quantity is shown in response to a user selecting a location in an image.

As an alternative or in addition to presenting a visualization, the radiation dose is transmitted. An image, warning, and/or quantity are transmitted. The transmission occurs while the radiation source applies the radiation, such as during the treatment period. The transmission is to a memory, network, server, or other computer. The transmission may be internal to a computer, such as transmitting a flag to trigger automated response to a warning. The results may be used for automatically generating detailed reports about the therapy. Such reports are used for planning, reporting, and/or for learning protocols for future therapy.

FIG. 5 shows a system 10 for assessment of radiation dose. The system 10 includes a memory 12, an x-ray source 16, a camera 18, a processor 26, and a display 28. Additional, different, or fewer components may be provided. For example, a network or network connection is provided, such as for networking with a medical imaging network or data archival system. As another example, multiple cameras 18 are provided. In yet another example, a C-arm or other robotic arm holds the x-ray source 16. A user interface may be provided.

The processor 26, memory 12, and display 28 are part of a medical therapy or imaging system, such as the fluoroscopy system 16, x-ray therapy system, or other system. Alternatively, the processor 26, memory 12, and display 28 are part of an archival and/or image processing system, such as associated with a medical records database workstation or server. In other embodiments, the processor 26, memory 12, and display 28 are a personal computer, such as desktop or laptop, a workstation, a server, a network, or combinations thereof. The processor 26, memory 12, and display 28 may be part of separate devices, such as the memory 12 being in an archival system, the processor 26 being in a therapy system or a server, and the display 28 being a phone or tablet.

The x-ray source 16 is an x-ray tube. A collimator and/or filter may be provided to controlling the distribution of the x-rays. The x-ray source 16 is configured to apply radiation to the patient 14. Based on the current, the intensity of the x-rays emitted by the x-ray source 16 is controlled. Shielding, an aperture or window, filtering, and/or collimation are used to control the distribution of the x-ray beam incident on the patient.

A C-arm or other robotic arm holds the x-ray source 16. The x-ray source 16 may be moved relative to the patient. This movement orients the x-rays relative to the patient.

The orientation, intensity, and beam distribution are fixed or may vary as a function of time. The therapy plan or parameters define the variance over time, such as providing a series of orientations with the same or different intensity and/or beam distribution being used at the different orientations. The dwell time at each orientation is the same or different.

The camera 18 is a CCD or other camera. Using structured light, acoustics, stereo view, or range camera, the camera 18 may detect the surface or a point cloud representing the surface of the patient 14.

The camera 18 is configured to image the patient during the application of the radiation. While the patient 14 is positioned on the bed, a trigger causes the camera 18 to capture a two or three-dimensional image of the patient 14.

The processor 26 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for registering, estimating locations, modeling dose, and/or generating visualizations. The processor 26 is a single device or multiple devices operating in serial, parallel, or separately. The processor 26 may be a main processor of a computer, such as a laptop or desktop computer, or may be a processor for handling some tasks in a larger system, such as in a therapy system. The processor 26 is configured by instructions, design, hardware, and/or software to be able to perform the acts discussed herein.

The processor 26 is configured to estimate locations of organs based, at least in part, on the image from the camera 18. The image is processed to estimate the locations of the organs. The processor 26 may determine the locations of landmarks to determine the position of the patient 14 relative to the x-ray source 16 and/or to determine characteristics of the patient. The characteristics of the patient are used, with or without characteristics input from other sources than the image, to estimate organ position (e.g., location and/or size) relative to the patient 14. The processor 26 automatically determines the organ position relative to the x-ray source 16 during the application of radiation by the radiation source 16.

Given the radiation parameters, the processor 26 is configured to model dosage of the organs of the patient. Based on the organ position or positions and the therapy parameters, the dose applied to the organ is estimated. Any estimation may be used, such as estimating with a physics-based (e.g., Monte-Carlo) or machine-learnt classification model.

The processor 26 models the dosage during the application of the radiation using the locations of the organs. The dose delivered to the organ is estimated more accurately based on the estimated position or positions of the organ over time during the treatment. The dose may be monitored as the radiation is applied or in a given appointment for therapy.

A visualization is generated by the processor 26. The modeled dose or doses are imaged. The image is of a spatial distribution of dose, such as dose by voxel or organ. The image may be part of an augmented reality view. Alternatively, the image is of a warning or text, such as a quantity-representing dose for an organ.

The display 28 is a monitor, LCD, projector, plasma display, CRT, printer, or other now known or later developed devise for outputting visual information. The display 28 receives images, graphics, or other information from the processor 26 or memory 12.

The display 28 is configured by the generated image in a display buffer. The display 28 is configured to display the dosage for at least one of the organs.

The memory 12 is a graphics processing memory, a video random access memory, a random access memory, system memory, random access memory, cache memory, hard drive, optical media, magnetic media, flash drive, buffer, database, combinations thereof, or other now known or later developed memory device for storing data or video information. The memory 12 is part of a therapy system, part of a computer associated with the processor 26, part of a database, part of another system, a picture archival memory, or a standalone device.

The memory 12 stores data used by the processor 26. For example, therapy parameters, camera images, calibration, registration, calculated transforms, organ position, look-up table relating landmark positions to organ position, landmarks, modeled dose, models, or other data are stored. Any data used, input to, output by, or created for the acts discussed herein may be stored in the memory 12 or another memory.

The memory 12 or other memory is alternatively or additionally a computer readable storage medium storing data representing instructions executable by the programmed processor 26 for assessment of radiation dose. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for assessment of radiation dose, the method comprising:
    applying radiation with an x-ray source directed to a region in a patient over a treatment period of a therapy appointment;
    estimating an anatomy position of anatomy of the patient;
    modeling dosage of the applied radiation at the anatomy of the patient, the modeling occurring during the treatment period while the patient is continuously on a same bed and using the anatomy position; and
    presenting a visualization of the dosage during the treatment period.

2. The method of claim 1 wherein applying the radiation comprises applying the radiation with a C-arm supporting the x-ray source and moving the x-ray source to different positions relative to the patient during the treatment period.

3. The method of claim 1 further comprising capturing with a camera an image of the patient during the therapy appointment, the image capturing a surface of the patient.

4. The method of claim 3 wherein capturing comprises capturing with the camera being a depth camera with a known position relative to the x-ray source.

5. The method of claim 1 wherein estimating the anatomy position comprises:
    determining a pose and size of the patient; and
    estimating the anatomy position from the pose and size.

6. The method of claim 3 wherein estimating the anatomy position comprises identifying one or more landmarks of the patient in the image, and estimating the anatomy position from the one or more landmarks.

7. The method of claim 1 wherein estimating the anatomy position comprises estimating a size of an organ.

8. The method of claim 1 wherein estimating the anatomy position comprises estimating from an atlas.

9. The method of claim 1 wherein modeling comprises modeling with a Monte-Carlo model implemented with parallel processing.

10. The method of claim 1 wherein modeling comprises modeling with a machine-learnt classifier.

11. The method of claim 1 wherein modeling during the treatment period comprises modeling prior to termination of the treatment period, the modeling based on the applying of the radiation in the treatment period up to a time of the modeling.

12. The method of claim 1 wherein presenting comprises generating an image representing the dosage.

13. The method of claim 1 wherein presenting comprises warning when the dosage is at or above a threshold level.

14. The method of claim 1 wherein presenting comprises presenting in an augmented reality view of the patient.

* * * * *